United States Patent [19]
Skiffington et al.

[11] Patent Number: 5,827,675
[45] Date of Patent: Oct. 27, 1998

[54] TEST APPARATUS, SYSTEM AND METHOD FOR THE DETECTION OF TEST SAMPLES

[75] Inventors: Richard Skiffington, Everett; Eliezer Zomer, Newton, both of Mass.

[73] Assignee: Charm Sciences, Inc., Malden, Mass.

[21] Appl. No.: 619,586

[22] PCT Filed: Jan. 2, 1996

[86] PCT No.: PCT/US96/00524

§ 371 Date: Mar. 26, 1996

§ 102(e) Date: Mar. 26, 1996

[87] PCT Pub. No.: WO97/03209

PCT Pub. Date: Jan. 30, 1997

Related U.S. Application Data

[60] Provisional application Nos. 60/001,081, Jul. 12, 1995 and 60/007,585, Nov. 27, 1995.

[51] Int. Cl.⁶ .............................. C12Q 1/66; C12M 1/30
[52] U.S. Cl. .......................... 435/8; 435/30; 435/287.6; 435/287.7; 435/288.2; 435/288.7; 435/309.1
[58] Field of Search .................. 435/8, 21, 29, 435/32, 34, 30, 39, 287.4, 287.6, 288.1, 288.2, 288.7, 307.1, 309.1, 808, 810; 422/58–61, 52; 600/572

[56] References Cited

U.S. PATENT DOCUMENTS

| | | |
|---|---|---|
| 3,713,780 | 1/1973 | Shapiro . |
| 3,776,220 | 12/1973 | Monaghan . |
| 4,099,920 | 7/1978 | Heiss . |
| 4,150,950 | 4/1979 | Takeguchi et al. ................ 422/102 |
| 4,239,745 | 12/1980 | Charm . |
| 4,239,852 | 12/1980 | Charm . |
| 4,353,868 | 10/1982 | Joslin et al. . |
| 4,409,988 | 10/1983 | Greenspan . |
| 4,707,450 | 11/1987 | Nason . |
| 4,770,853 | 9/1988 | Bernstein . |
| 4,774,173 | 9/1988 | Reinhartz .................... 435/32 |
| 4,806,415 | 2/1989 | Fossati ....................... 435/21 |
| 4,929,546 | 5/1990 | Mayra-Makinen ............. 435/32 |
| 5,077,200 | 12/1991 | Habenstein ................. 435/21 |
| 5,200,311 | 4/1993 | Charm et al. . |
| 5,223,401 | 6/1993 | Foltz et al. . |
| 5,223,402 | 6/1993 | Abbas et al. ................. 435/21 |
| 5,238,649 | 8/1993 | Nason . |
| 5,266,266 | 11/1993 | Nason .......................... 422/58 |
| 5,283,180 | 2/1994 | Zomer et al. . |
| 5,354,663 | 10/1994 | Charm et al. . |
| 5,374,535 | 12/1994 | Zomer et al. . |

FOREIGN PATENT DOCUMENTS

| | | |
|---|---|---|
| 155747 | 9/1985 | European Pat. Off. . |
| 0 309 429 | 3/1989 | European Pat. Off. . |
| 0 592 503 | 4/1994 | European Pat. Off. . |
| 93/09431 | 5/1993 | WIPO . |
| 9525948 | 9/1995 | WIPO . |
| 9614570 | 5/1996 | WIPO . |

OTHER PUBLICATIONS

U.S. Dept. of Agriculture, *FSIS Directive 7370.2*, pp. 1–8, Jun. 28, 1995.

Charm Sciences Inc. in collaboration with Vienna Beef, "HACCP Friendly Testing System" (5 pp) No Date Provided.

(List continued on next page.)

*Primary Examiner*—William H. Beisner
*Attorney, Agent, or Firm*—Richard P. Crowley

[57] ABSTRACT

The invention concerns a test apparatus for the testing of a test sample on or in a material, such as body fluids or food, particularly adapted to a bioluminescent test, such as for the detection of ATP or phosphatase or other materials. The test apparatus includes a transparent tube having at one end a sample unit and at the other end a detachable or nondetachable test unit which are connected, and which includes a cover with a probe containing a swab at one end. The test apparatus includes probe positioning marks on the exterior of the sample unit, so that the probe may be moved between selected test positions, and as it moves from a non-use to a use position, various test reagents which are sealed within the test unit are punctured by the probe, and the test sample and the test reagents are reacted together in the test unit.

22 Claims, 5 Drawing Sheets

OTHER PUBLICATIONS

Lighting product brochure, IDEXX Laboratories, Inc., Feb. 1995 Davis, Carl E. et al, "Rapid Fluorometric Analysis of Acid Phosphatase Activity in Cooked Poultry Meat", Journal of Food Protection, vol. 57, Dec. 1994.

BioOrbit *Handbook of ATP–Hygiene Monitoring*, "A guide to the effective use of the Bio–Orbit Hygiene Monotoring System".

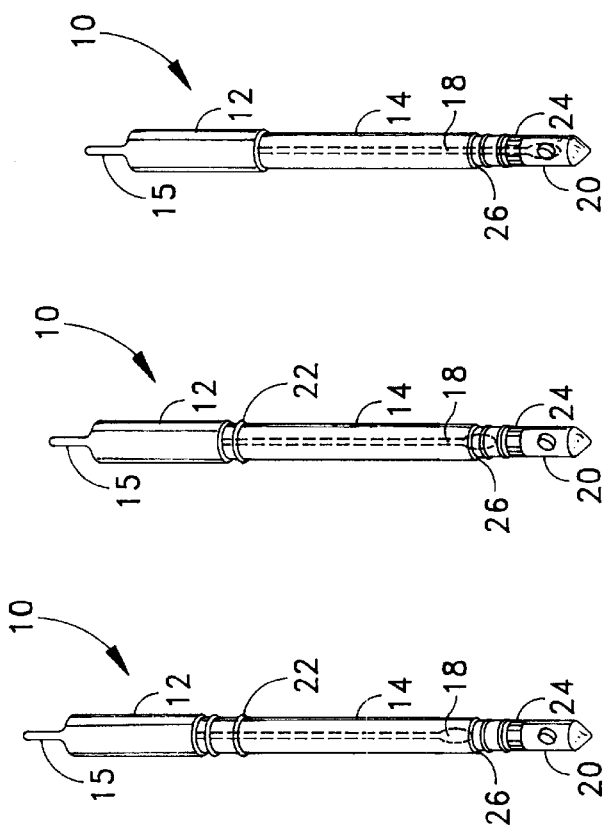
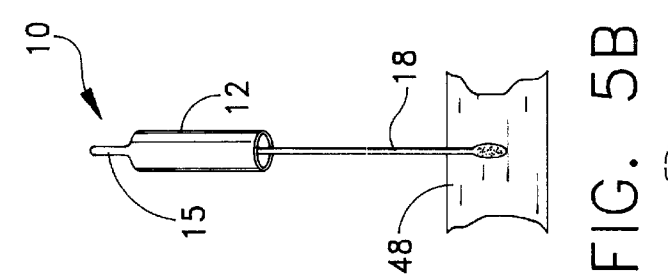
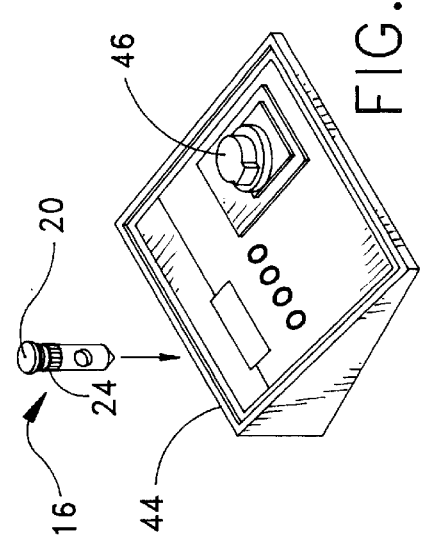
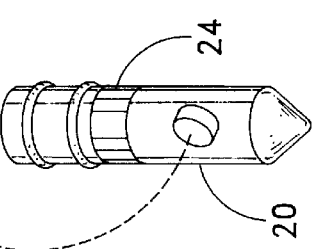
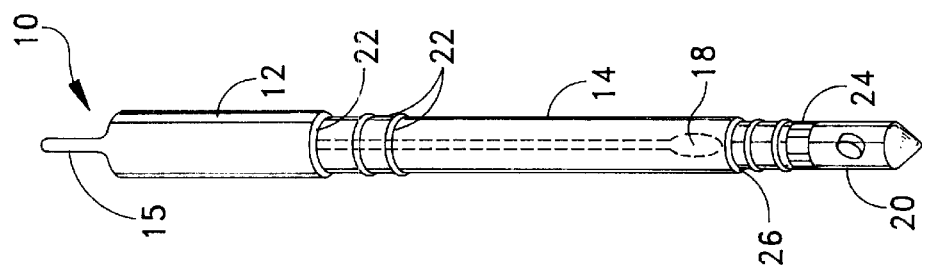

TEST APPARATUS, SYSTEM AND METHOD FOR THE DETECTION OF TEST SAMPLES

DESCRIPTION

REFERENCE TO PRIOR APPLICATIONS

This application claims the benefit of provisional U.S. patent application Ser. No. 60/001,081 filed Jul. 12, 1995, and also the benefit of provisional patent application Ser. No. 60/007,585, filed Nov. 27, 1995.

BACKGROUND OF THE INVENTION

It is desired to provide for a rapid and efficient test for the detection of various test samples from materials or surfaces. Various test apparatuses and test methods have been developed for that purpose. For example, it is widely desirable to determine or to test through quantitative and qualitative tests body fluids, such as blood, and urine, and milk and the like, as well as food, such as meat products, fruit, vegetables, and to detect for alkaline phosphatase, salmonella, drugs, and antibiotics, such as; for example, sulfa drugs, beta-lactam drugs, organophosphates, carbamates and active metabolites, various bacteria and pathogenic combinations, either in materials or on the surface of materials, or both.

For illustration only, the detection and characterization, qualitatively and qualitatively, through the employment of a color change or a bioluminescence test, for the detection of the alkaline phosphatase, such as for example, the detection of ATP on or in materials, is most desirable for providing a measure of immunoeffectiveness, so that a rapid determination can be made of whether a processing or surface area is adequately hygienically clean and free of, for example, alkaline phosphatase, so that corrective or disinfectant action can be instituted.

Typically, the detection of ATP is by bioluminescence assay, which is a standard test which will detect food residue, bacteria, yeast, mold, by measuring the ATP on a surface. The method comprises obtaining a test sample, for example, on the surface of the material, such as by non-laboratory or out-of-laboratory or at field locations, the activating of the test sample in the presence of test reagents, and then later employing a luminometer to determine test results, which can be compared with a controlled sample or controlled environment.

The detection of a phosphatase, like ATP, may be made in a dimensional color test and method. However, such a test is time consuming and requires laboratory trained personnel. The present commercial tests are generally directed to a bioluminescence test, which ordinarily takes less than five minutes and employs premeasured and prepackaged separate test reagents and employs a luminometer to detect test results. Generally, a portable luminometer, as used in the field, with the use of test containers, such as various test tubes or plates. The concentration of the phosphatase has been determined by measuring or counting of the bioluminescence, determined by the reagents mixing with the test sample, and comparing the count against certain accepted control standards, or a threshold of a control standard.

There are various ATP tests available in the field, and one bioluminescent ATP monitoring test in present use is described in "The Handbook of ATP-Hygiene Monitoring" by Bio-Orbit Oy of Turku, Finland, while another luminescent ATP hygiene monitoring test in use is called the Charm ABC Swab Test™, sold by Charm Sciences, Inc., of Malden, Mass., both of which tests and literature are hereby incorporated by reference.

Another portable swab-type device for use in an ATP bioluminescent test for measuring cleaning effectiveness is distributed under the mark Lightning™, swab device by Idexx Laboratories, Inc., of Westbrook, Me. (Lightning™ is a trademark of Idexx). The Lightning™ device consists of an integral swab design, which contains a unit dose of reagents in use with a portable luminometer. The device employs an elongated tube with a cover on it at one end and an elongated, extended premoistened wetting agent on a premoistened swab, and with such end containing a buffer in a bulb, while the opposite read chamber end, where the test results are read, comprises a glass ampoule. The ampoule contains a luciferin and luciferase reagent material, with a glass ampoule separating the read chamber from the buffer end. The swab is removed from the tube and is used to obtain a test sample from a surface to be tested for ATP, and then the swab is reinserted within the tube.

The cover end of the device is then bent and squeezed to force out the buffer solution, while the opposite end containing the glass ampoule with the reagents, is crushed by the user so that the buffer solution and the released luciferin-luciferase test reagents are then admixed within the tube with the test sample to form the reaction mixture, which would provide for the appropriate bioluminescence. The read chamber at one end is inserted into and read by the portable luminometer. Thus, the Lightning™ device provides a swab-type test probe requiring the bending and squeezing of one end and the crushing of a glass ampoule at another end of the device, then the admix of the materials prior to inserting the read chamber into a luminometer and then reading the test results. The Lightning™ swab device, together with its test methods, literature and equipment, is hereby incorporated by reference.

It is desirable to provide for a new and improved test apparatus, system and method adapted for use with a wide variety of known and unknown test methods for the detection of test materials on a material or on a surface. The improved test apparatus is greatly simplified in structure and is effective in use, eliminates possible operational mistakes by personnel in the field, does not require separate pipettes and test tubes, does not provide for the crushing of glass ampoules with its inherent danger, and provides excellent separate stability of test reagents which may be employed with the test results by specifically prepackaging the reagents, so that the test apparatus may be stored for long periods of time prior to use.

The device is particularly adapted for in-field or out of the laboratory testing by unsophisticated personnel, as well as the use by laboratory personnel, and further and importantly may have the test results determined by using the entire test results in one end thereof, or removing one end of the test unit for testing in a test instrument, which may be, for example, a visual change of color, or other property, in some tests, a use of a portable luminometer, or the use of other types of test instruments including radioactive detection devices, either alone or in any combination. The improved test device is particularly adaptable as a disposable, inexpensive, transparent, plastic pocket test apparatus.

SUMMARY OF THE INVENTION

The present invention concerns a test apparatus and a test system employing the test apparatus, and a test method employing the test apparatus and system, and in particular in one embodiment is directed to a bioluminescent type test for the detection of test samples from a material or material surface, by employing known test techniques.

The invention comprises a test apparatus composed of a sample unit and a test unit, which sample and test units may be generally longitudinally aligned and secured together generally in tubular form, and which may be integral or may be disposed for the removable detachment of the test unit by the user. The test apparatus is employed for the detection of the qualitative or quantitative, or for any analytical test of one or more test samples from or on a material or on a material surface.

The test apparatus comprises a sample unit having a probe means, such as an elongated element having a first and second end, with the first end adapted to obtain a test sample with a test collection swab or means at one end, and generally would comprise a probe-type collection means at one end, by which a test sample may be collected, and a sterile chamber having a first and second end and adapted to receive and retain therein prior to use, and optionally after use, the said probe means, and having a cover for the first end of said chamber to seal the end of the chamber.

The sample unit also includes means to retain said probe means within said chamber prior to use; that is, to render the test apparatus sterile prior to use, and without indiscriminate movement of the probe means within the chamber. The sample unit also includes a probe positioning means, comprising a plurality of selected identification positions between the probe means and the chamber in order to identify the relative position of the probe means, and particularly the first test end of the probe means, within said chamber or within said test units, both before and after use. The sample unit also includes means to move a cover end, having the probe means move generally longitudinally to the first end of the probe means, in relationship to said chamber, typically over or within said chamber for use, to one, or typically a plurality of, selected identification positions as required in the particular test method and apparatus.

The test apparatus also includes a test unit attached to a sample unit, generally longitudinally aligned and attached to the sample unit and having at its bottom end a reagent housing, which is optionally generally transparent, so that a luminometer or visual test result observation may be made, and having a first end and second bottom end, the first end attached to said second end of the chamber in the sample unit. The test unit is adapted for use alone or integrally with the test apparatus, so that the test results may be observed in the reagent housing, or the reagent housing may be detached and used in a test instrument, or to conduct tests on the admixture therein, or the entire test apparatus, together with the reagent housing, employed in a test instrument, such as the bottom end placed in a luminometer or other instruments for the detection of the test sample.

The test unit also includes a test sample reagent means, which comprises preselected reagents depending on the desired test to be carried out, and when one or more tests may be carried out alone or in any sequence as desired, with the test reagent means designed to contact the test sample collected. The reagent means generally comprises at least one sealed reagent package containing a test reagent, which may be solid, liquid, powder, emulsion, suspension, tablet or substantially any combination separately or admixtured thereof.

There may be and usually is a plurality of separate sealed reagent packages, depending on the particular test method selected for the test sample. The test sample reagent means is characterized as being adapted, arranged and constructed, so as to be displaced, punctured, penetrated or unsealed by the longitudinal movement of the first end of the probe means to a selected identification position, so as to permit the admixture or combination reaction or otherwise contacting the test sample on the probe means, and the one or more reagents which have been released from the sealed reagent action of the reagent means.

Generally, the reagent means is characterized by a package having a puncturable foil seal or membrane, which is adapted to be penetrated by the movement of the probe means, or by other means after collection of the test sample by the probe means, and with the one end of the probe means moved to a selected identification position, so as to generally sequentially, puncture the aligned, sealed reagent packages in the sequence as desired. The puncturing occurs at progressive, selected identification positions, usually which positions are marked on the outside of the chamber for easy observation by the user. In some test methods, as desired or required, sequentially contacting of test reagents is desired, while in other tests the sequence is not of importance. Generally the reagents are also packaged and separated in order to provide for better storage life. Generally, two, three, four, or five or more test reagents or combinations in a package are employed, and would include, for example, at least one liquid reagent, either water or a buffer solution or a neutralizing solution, and then one or more powdered or tablet type packages, so that as the test sample on the probe means is pushed downwardly, it comes in contact with each of the selected reagents, with the test reagents and test samples admixed at the bottom end of the housing of the test unit. A test reagent, packaged or unpackaged, may also be placed in the bottom end of the test unit, such as a solution or tablet to be admixed with the other reagents and test samples.

The test apparatus, containing the sample and test units, is composed, for example, of an elongated thermoplastic, transparent, flexible, plastic (like polyethylene) tube, having a cover, with an elongated semi-rigid probe exposed within the sterile chamber of the tube, and a transparent test unit end at the other end and containing therein the prepackaged test reagents. This apparatus is well adapted for use in the field by generally untrained personnel to obtain test samples from or in a wide variety of materials. The test apparatus may be composed of a disposable, transparent tube material that is easily carried by a user in a pocket or briefcase to the field or plant as required, and usually may be disposed of in toto, or where the test unit is removed from the bottom and then is sealed, may be used in a portable luminometer, which thus makes disposal of the test apparatus quite easy, without undue contamination of the atmosphere.

Generally, the probe means comprises an elongated, somewhat flexible, usually semi-rigid plastic element secured at second end to said cover, and which cover is mounted over the one end of the chamber, typically slidably, but also for removable, helical or other longitudinal movement within the chamber. The probe means contains a test sample collection material secured at the one end, such as, for example, a fibrous type material such as a cotton swab, which may, if desired, be premoistened, such as by a water or an aqueous wetting solution, or with other compositions such as color indicators, dyes, reagents or test reagents, or merely may contain chemicals which physically or chemically bind to the material to which the test is directed. Generally, the first test end of the probe means is liquid-moistened, such as by water or a wetting agent solution, particularly when it is used for the collection of test samples on materials or surfaces, to determine hygiene cleanliness, in order to aid in the collection of the test sample on the surface.

The test apparatus is provided to the user with a sample and test units together and with the sterile probe means within the sterile chamber of the sample unit. The probe means is originally in a non-use position, so it does not longitudinally move until after the collection of the test sample by the user. The probe means is then moved sequentially to the selected identification positions. Optionally and preferably the test apparatus includes some means to retain the probe means in the original, selected non-use position, prior to use by the user, such as the use of an adhesive tape wrapped about the one end of the cover and the chamber, which is user removable, or the use of an easily breakable adhesive, or the use of a heat shrinkable material, such as a transparent plastic material which may be shrunk around the one end of the cover and the chamber or the entire test apparatus to render it sterile until use, to preposition the probe means within the sterile chamber prior to use.

The test apparatus includes probe position means, in relationship between the sterile chamber and the one end of the cover containing the probe means, in one acceptable and preferential method of use. The probe position means generally would comprise any type of means by which the one end of the cover containing the probe means is moved longitudinally in relationship to the test unit which contains the reagent means. Thus, in one example and preferably, the chamber may contain a series of spaced-apart, generally parallel identification lines or marks, either marked by colors or numbers or both, or by some identification means, whereby the bottom portion of the cover containing the probe means and prior to the removal of the retaining means is prepositioned, and then user-moved relative to the marks on the chamber.

The test instructions then permits the obtaining of the test sample using the probe means on a material or a surface, and reinserting the probe means within the chamber, to a selected, usually first non-use, non-reagent identification mark, or in the one end of the probe chamber, and does not extend beyond the second end of the chamber, that is, the test end is above the test unit. The probe position means then provides for the longitudinal, slidable or helical movement of the cover means with the test probe, to say, a second position, third or fourth or multiple positions, whereby the one end of the probe means then contacts the respective reagent test means positioned in the test unit. This provides for contact of the test sample of the probe means with the test reagents, so that all of the test samples or reagents are then contained and admixed within the test unit at the one bottom end of the test apparatus. Generally, the final probe position means is such that all of the test reagent unit means have been punctured down at the one end, and the one end of the probe means is disposed slightly within the test unit. The probe may then be twirled to ensure good contact with the reagents, and then withdrawn to the original or a non-use position within the chamber for later use or disposal. Typically, the sample unit is within the chamber, so that the test apparatus, with the sample unit, the sample and test unit all together may be readily and easily disposed of in an acceptable manner.

The position probe means should be well-marked and typically uncomplicated, so that the probe position means may be easily understood and used by people in the field.

The means to move the one end of the probe means may vary; so long as the probe means is moved longitudinally within the chamber between non-use and selected use positions, and from the one end of the chamber into the test unit, for example, by the employment of a slidable longitudinal movement, when the cover is placed in a snug, close-fitting sliding position over the one open upper end of the chamber of the sample unit, or where there are helical or spiral grooves placed on the inside of the cover, or on the outside of the chamber unit or both, to provide for the spiral movement to a selected probe position means, or where merely bumps or other means are employed so that the user may move the probe means easily to the selected positions.

Of course, it is also recognized that where there is only a test sample at the end of a probe and only one reagent, it may well be that no probe position means are required, other than for use or non-use, and the probe merely, after a test sample is placed in the chamber, and merely longitudinally moved downwardly to contact a single reagent to force the reagent then to contact the test sample directly into the test unit for test or observation. This would indicate the use of a very simple test method, and typically would not lend itself, for example, to the bioluminescent-type method for determining enzymes like phosphatase, or for the use of beta-lactams, or in processing of meat, or for determining sulfa, drug residues or organophosphate residue on products.

In another embodiment, the test apparatus may comprise a single tube with a cover, wherein the entire test apparatus, after the test sample on the longitudinal movement of the probe means, is employed in its entirety in determining the test results, that is, the test unit is not made to be detached or removable from the one end of the sample unit, but is for example, securely attached thereto, for example, by being integrally molded therewith. In such a situation, the test unit at the one end can still be inserted into a luminometer, or other test instrument, and the color or other change affected by the test results observed or read. Thus, as desired, the entire test apparatus can be disposed of in an effective and environmentally non-toxic manner.

In another embodiment, which will be illustrated, the test unit at the one end of the test apparatus can be detachably removed in any manner thereto, such as employing threads, or slidably fit, or a weakened mechanical section or other means, or merely just taping the units together, so that after movement of the probe to selected identification positions, then the removal of the probe means to the non-use position, the test unit at the one end of the test apparatus may be easily twisted or removed by the user, and would then contain therein the test samples of the various reagents, in an admixture. In this particular method of operation and structure, the test unit, which occupies only a small volume at one end, may then be detached and inserted, for example, into a portable field-type luminometer, so this test method lends itself quite readily to the use of portable test instruments and use in the field or non-laboratory environments. Where this test method is employed it is often desirable to provide a means to seal the one open end of the test unit after removal from the test apparatus. This can be accomplished by a variety of means; for example, by employing a screw-type or plug-in type cap secured to the test apparatus, or by more conveniently using a removable adhesive detachable seal, for example, which may be secured to the test apparatus and readily removed by the user after detachment of the test unit, and then placed over the open end of the test unit and wrapped around to cap the open end of the test unit. Such a seal, for example, may comprise but not be limited to: an aluminum foil, which is adhesively sealed on one side, or any other means to cap, seal or otherwise secure the one open end of the test unit.

It is sometimes desired to provide, rather than a generally cylindrical tube for the test apparatus, a tube wherein the plastic is flexible, particularly toward or near the one of the test unit, so that a user may then squeeze the one end of the tube generally intermediate the test unit and the sample unit, so as to insure the test sample on the probe means is squeezed out together, for example, with the premoistened reagent liquid and contacts the test reagents fully before the one end of the squeezed, used probe means is withdrawn into the chamber.

The reagent housing which is used generally is transparent, particularly where a visual observation is desired; however, it is recognized that the reagent housing may be non-transparent, particularly where the particular test to be carried out does not require transparency of the housing or test unit. The test sample reagent means, which is placed generally in the test unit or in the chamber adjacent the open end of the test unit, is adapted to be punctured or pushed by one end of the probe, and provides powdered, liquid, tablet or suspensions of one or more or a combination of chemicals, materials and reagents to the test unit as desired by any particular test.

Usually, the test reagents would generally comprise from two to five separate sealed reagent packages, at least one or more of which packages would be a liquid package, such as a water or buffer solution or a saline solution. It is desirable to place in at least one of the test sealed reagent packages an individual dye or combinations in each package, so that the user is insured that the test probe punctures each package and that the dye color is present in the reagent housing.

Generally, for example, the sealed reagent package, particularly where the test unit is generally cylindrical, would comprise a plurality of spaced apart, separately sealed test reagents containing one or more test reagents, the package so designed, so as to be penetrated, punctured or dispersed by one end of the probe means on longitudinal movement, to provide for contact between the contents of the package and the test sample. The probe means penetrates a puncturable or rupturable membrane, which is placed on at least one side, and typically on opposing sides of a generally cylindrical package, or in fact where a tablet is used, is designed to break up a powdered tablet, in contact with the liquid solution and the test sample.

Generally, the sealed reagent package comprises a plurality of generally separate, individual packages with one or more test reagents having puncturable sealed membranes and opposite radial sides thereof, all selected to be punctured at selected identification positions by the probe positions, to provide for adequate contact between the test sample at the end of the probe means and each of the reagents, so that the entire mixture or content thereof, would end up in the reagent.

The number, type, material concentration and form of the test reagents in each package, or alone, may widely vary. For example, the test reagents may contain a dried microorganism or other microorganisms, growth and enhancing indicators, such as detergents, ethylene diamine, tetraacetic acid, enhancing reagents to enhance the test results, such as pH or dye color indicators, buffer solutions, saline solutions, water solutions, enzymes, material which bioluminesces, such as luciferin alone and in combination with a luciferin derivative, or with other materials which provide biolumination, as well as low level radioactive isotopes, for example a beta-lactam test, stabilizers, antioxidants, phosphatates and phosphatase substrates, various biological buffers, material such as a chromogen which acts in the presence of an enzyme, and a wide variety of other materials.

The test apparatus, for example, may be used in test methods to determine phosphatase, ATP, beta-lactams, pesticides, bacteria such as coliform and E. coli, etc (see, for example, tests described in U.S. Pat. Nos. 4,239,745, 4,239,852, 5,200,311, 5,283,180, 5,354,663, and 5,374,535, incorporated herein by reference.

The invention comprises a method for the detection of a test sample from or on a material, which method includes providing a test apparatus with a sample and test units, collecting a test sample by use of a probe means which is stored in a sterile chamber within a sample unit, and thereafter using the probe means, for example, containing a test swab with an end thereof, which may be premoistened so as to collect a test sample. Thereafter, the method includes using the probe means within a chamber to puncture one or more test reagent means, so as to provide for contact within a test unit at one end of the test apparatus of the test samples with one or more test reagents, so that the test method can be carried out, and with the probe moved longitudinally between selected probe positions within the test apparatus.

The method also includes employing a test unit, either individually or by the use of instruments, either alone or as an integral part of the test apparatus, to do the test detection. Any test method may be typically employed in the test apparatus, the selection of a particular test and test reagents known to persons skilled in the art depending on the particular test.

The apparatus is composed of two units, the sample unit and the test unit. In one embodiment, the test unit is an integral part of the apparatus and does not need to be removed for final reading of results. Instead, the whole apparatus is inserted to the luminometer for reading. Another embodiment, which calls for removal of the test unit for analysis, may be used because of the portable luminometer constraints. The analyzer, e.g. luminometer, can accommodate the whole apparatus, and therefore better and more simply contain all chemicals in the apparatus for disposal. The cover/chamber sliding mechanism can be controlled after testing by a spiral or raised portion on the plastic in order to control the position and/or speed of or stop the downward motion of the probe, and control the timing for each chemical reaction. Some tests will require the use of a timer to allow the full reaction to take place on a timed basis.

The sample unit contains a sterile chamber housing the probe, made of disposable plastic and composed of a chamber cover that holds the probe and the chamber for the probe, which can be made of metal or other materials. The cover and chamber are sealed prior to use to prevent downward movement of the cover, moving the probe into the chamber. A simple sealing mechanism is used, such as heat shrink plastic or paper that can be torn by a simple twist, to open the chamber and cover and retrieve the probe for sampling.

The chamber is comprised of a waterproof housing to enable the probe material to be maintained moist with the proper solution and ready to use.

The probe may be a swab-type device, made of plastic, wood or metal, with the tip made of absorbent material such as cotton, or synthetic material (plastic), or a hollow tube; e.g., a disposable pipette. The tip may be used to obtain a sample by a capillary or vacuum suction, or an affinity probe that can adsorb the analyte by bioaffinity binding; e.g., antibodies or receptors, may also be used.

The unit may also contain instructions and a control mechanism, by which the probe, after the sampling step, is inserted into the testing unit and longitudinally moved to puncture the membranes and allow penetration of each reagent container.

In an optional embodiment, a squeezing mechanism may be desired for full recovery of the sample and products of the interaction of the sample and the reagents. In this embodiment, the chamber's opening is narrowed to enable the swab, when withdrawn to the non-use position, to squeeze out all liquids into the test microtube for best recovery of color/luminescence products, or a flexible plastic tube squeezed about the probe means capping the apparatus.

The test unit is essentially a transparent test tube (plastic or glass) that contains the active components of a selected test with the test sample. Each chemical is contained within a small cylinder; e.g. a reagent chamber, and inserted in the housing and both top and bottom are sealed with a water- and chemical-resistant membrane made of aluminum foil, plastic or waxed paper, or a combination of the above.

The membrane is thin enough to be fractured, burst, or punctured by the probe with a slight pressure by the user. The reagents are packaged in the reagent chamber in liquid, dried powder or tablet forms. The number of reagents may vary as required for each test method selected; for example, from one to five ingredients, depending on the test requirements.

Optionally, indicator dye is included with the early reagent (e.g. in the first Reagent A), the first penetrable reagent. This helps to verify that all the chemical interactions during the test are working properly. When the dye is visible in the test housing, it is an indicator of a used device.

The test apparatus system and method will be described for the purposes of illustration only in connection with a series of illustrative test apparatus and test method employing various test apparatus. However, it is recognized that those persons skilled in the art may make various modifications, changes, additions, and improvements to the test apparatus, system and methods without departing from the spirit and scope of the invention.

BRIEF DESCRIPTION OF THE DRAWINGS

FIG. 5, with schematic illustrations 5A–G, shows the steps of the test method employing the apparatus of FIG. 1.

DESCRIPTION OF THE EMBODIMENTS

Figure 1:
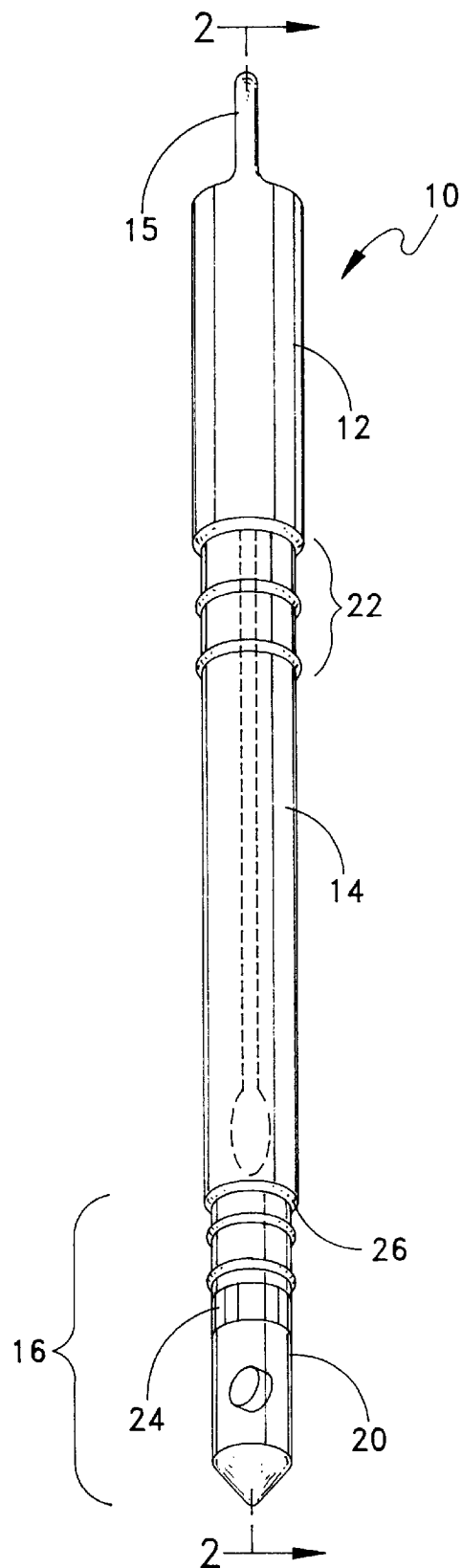
FIG. 1 is an elevational view of the test wand apparatus of the invention.

FIG. 1 shows the test wand apparatus 10, comprised of transparent, semi-rigid molded polyethylene, with cover/plunger 12 being secured around and outside of elongated sterile sample unit cylinder 14. A microtube test unit 16 is attached to the bottom end of the sample unit cylinder 14, the microtube test unit 16 having indentations 26 and finger grips 24 to enable a user to manually grasp and remove the microtube test unit 16 from the sample unit cylinder 14.

A swab 18 (shown in broken line) is inserted into the interior top end 15 of the cover 12 and removably secured therein. A generally circular aluminum foil seal 20 is positioned on the exterior surface of the microtube test unit 16 and is removably adhered by self-adhesive backing to the microtube 16. Indicator lines 22 are shown on the upper end of the sample unit cylinder 14. The bottom end of the cover 12 and the top end of the sample unit cylinder 14 are secured together with a heat-shrunk plastic seal 17, and removably secured around the periphery of the cover 12 and sample unit cylinder 14, to prevent downward movement of the cover 12 when the apparatus is in a non-use position.

Figure 2:
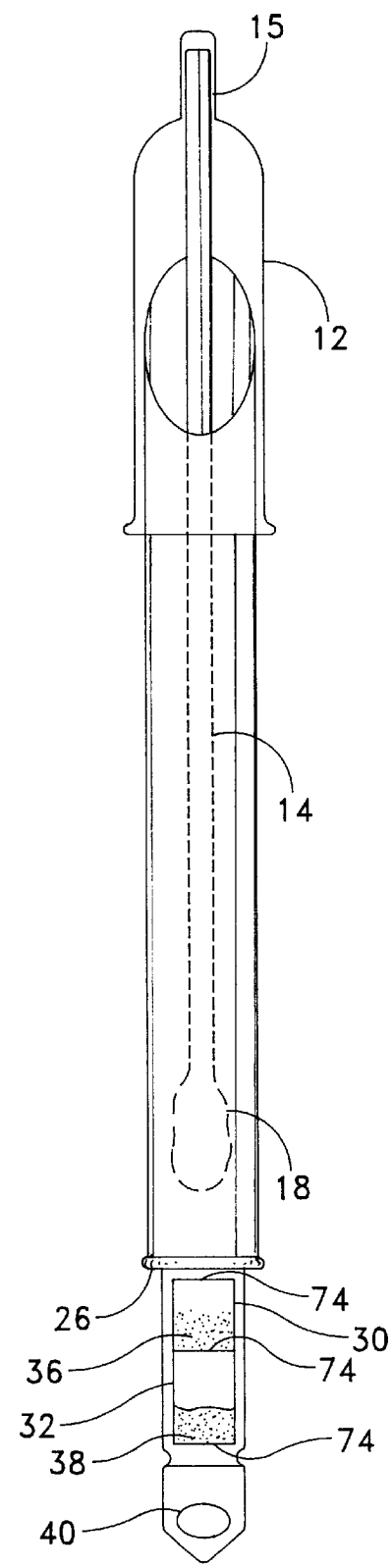
FIG. 2 is a sectional view along line 2—2 of the apparatus of FIG. 1.

In the sectional diagram of FIG. 2, the apparatus of the invention 10 is shown with the cover 12 having the swab 18 removably inserted into the interior of top end 15 of the cover 12. The top of the sample unit cylinder 14 is shown with an angular, elliptical cut 19 thereon. A swab 18 is inserted into the interior top end 15 of the cover 12 and removably secured therein. FIG. 2 also shows the microtube test unit 16 with inner containment system 49 having units 30 and 32 and space at the bottom 34, the units containing Reagent A 36, Reagent B 38, and Tablet C 40 respectively. Puncturable membranes 74, which separate each unit of the inner containment system 49, are also shown.

Figures 3, 4:
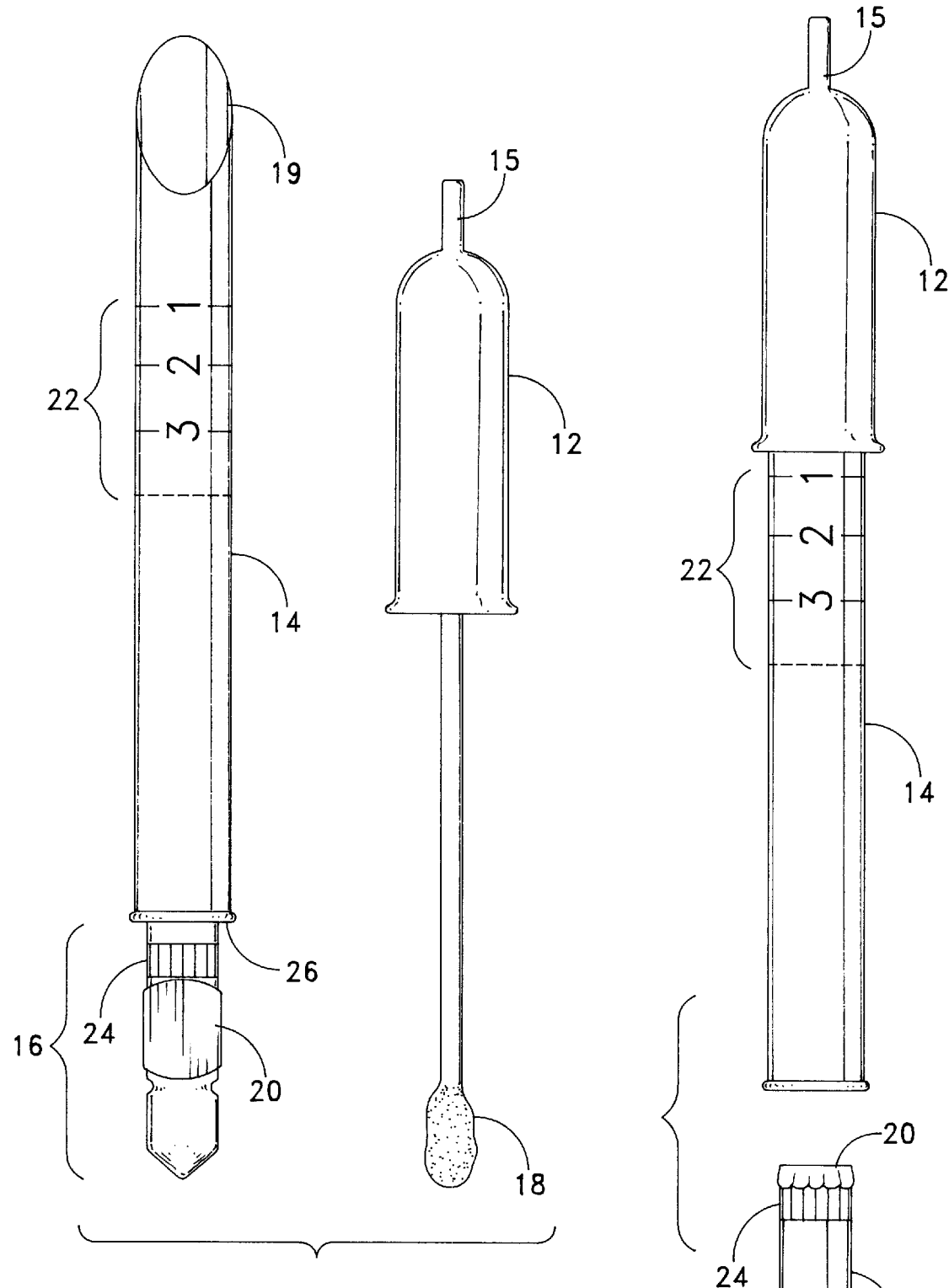
FIG. 3 is an elevational view of the apparatus of FIG. 1 with the plunger removed.
FIG. 4 is an elevational view of the apparatus of FIG. 1 with the microtube removed and capped.

FIG. 3 shows the apparatus 10 with the cover 12 removed from the sample unit cylinder 14, the microtube test unit 16 still attached to the end of the sample unit cylinder 14. A swab 18 is inserted into the interior top end 15 of the cover 12 and removably secured therein.

FIG. 4 shows the apparatus 10 with the microtube test unit 16 detached from the sample unit cylinder 14 and sealed a with the adhesive-backed, aluminum foil seal 20.

FIGS. 5A–F shows the apparatus 10 of FIGS. 1–4 in use. FIG. 5A shows the apparatus 10 prior to use, with cover 12, sample unit cylinder 14 and microtube test unit 16 attached. FIG. 5B shows the cover 12 withdrawn from the sample unit cylinder 14, with the swab 18 obtaining a test sample from surface area 48. FIG. 5C shows the cover 12 being reinserted into the sample unit cylinder 14, and being moved downwardly longitudinally to the first of the indicator marks 22. FIG. 5D shows the cover 12 being further depressed into the sample unit cylinder 14 at the second of the indicator marks 22.

FIG. 5E illustrates the cover 12 being depressed in a downwardly longitudinal manner fully within the sample unit cylinder 14 to moisten the tablet at the bottom of the microtube test unit 16. FIG. 5F shows the microtube test unit 16 after removal from the sample unit cylinder 14, with the adhesive-backed aluminum foil seal 20 being sealed over the microtube test unit 16. FIG. 5G shows the microtube test unit of FIG. 5F being inserted into a luminometer 44 and counted with a counter 46 for testing of the sample.

Figure 6:
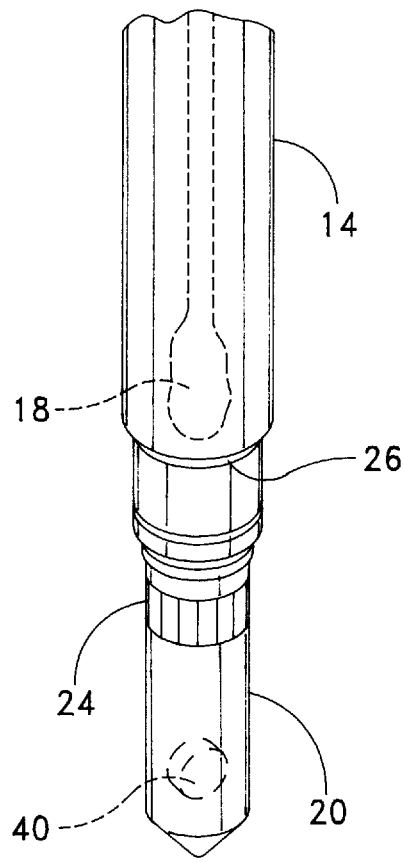
FIG. 6 is an enlarged, fragmented, sectional view of the lower section of the apparatus of FIG. 1 in the non-use position.

FIG. 6 depicts an enlarged view of the bottom end of the apparatus 10 with the microtube test unit 16. The swab 18, premoistened with swabbing solution, is moving longitudinally and downwardly toward the first prepackaged containment unit 30 with a microbial lysis solution and ATP stabilizer. The second prepackaged containment unit 32 is shown with the buffer optimized for luciferin-luciferase reaction, and the luciferin-luciferase Reagent tablet 34 is shown in the bottom of the microtube test unit 16.

Figure 7:
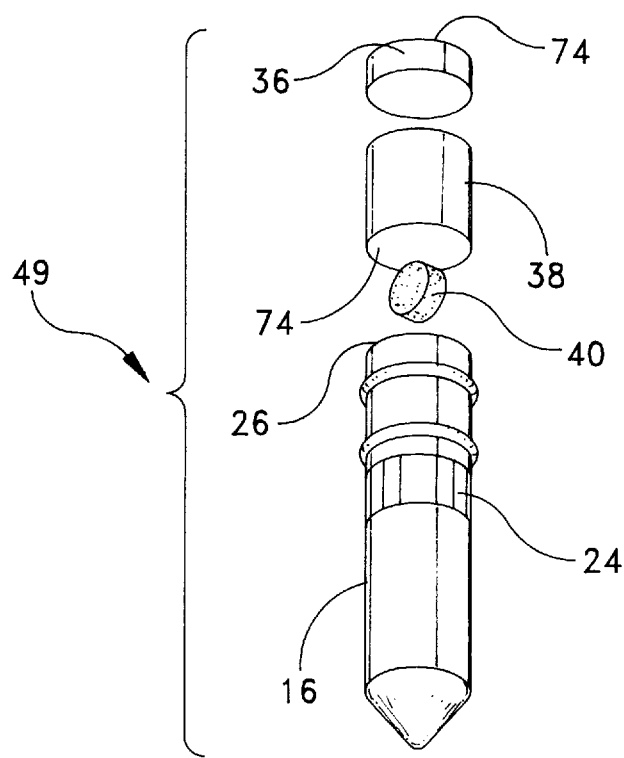
FIG. 7 is an enlarged, exploded, fragmented view of the microtube and reagent packages of the apparatus of FIG. 1.

FIG. 7 shows in further detail the single use sequential unit dose containment system 49, with plastic cylinders 30 and 32 containing Reagent A 36 and Reagent B 38. Tablet 42 is shown in position below the units. Puncturable membrane seals 74 for the separation of the containment units are also illustrated. The system 49 is shown prior to insertion into the microtube test unit 16. While in the preferred embodiment for the detection of ATP the above-mentioned reagents are utilized, it is recognized that other combinations of reagents and detection products may be used for specific alternate applications of the test apparatus as shown and described.

FIG. 8 illustrates another embodiment of the test apparatus 50, with cover/plunger 52 having a rounded top end and threads 56 on the interior surface of the open bottom end of the cover 52. These threads 56 are threadably fit to the threads 58 on the outside of the open upper end of the sample unit cylinder 54. A swab 70 is removably inserted into the interior of the top end of the cover 52. This embodiment also depicts a microtube test unit 60 removably secured to the sample unit cylinder 54 with a peripheral indentation 66 and finger grip 64 to enable the user to detach the microtube test unit 60 from the sample unit cylinder 54. A plastic heat shrunk seal 72 secures the sample unit cylinder 54 and cover 52, and an adhesive-backed aluminum foil seal 62 is removably secured to the exterior surface of the microtube test unit 60. The aluminum foil seal 62 is used to cap the microtube test unit 60 in a secure fashion after it is detached from the sample unit cylinder 54 for testing. Indicator lines 68 allow the user to control the turning of the cover 52 with the threads 56 to enable the swab 70 to be longitudinally downwardly inserted into the prepackaged reagent containment system 60.

Figures 8A, 8B:
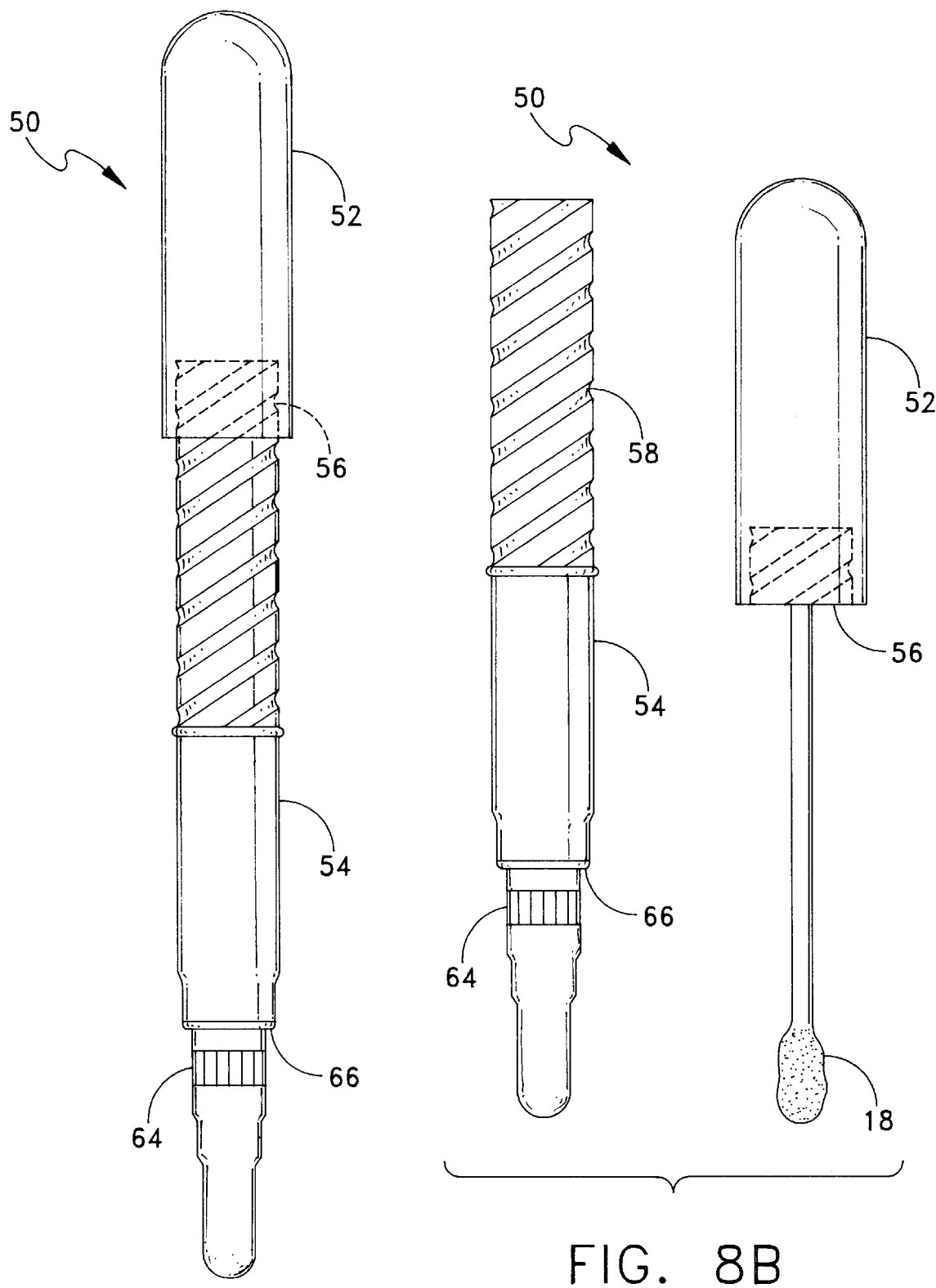
FIGS. 8A and B is an elevational view of another embodiment of a threadable test wand apparatus of the invention, with FIG. 8A showing the apparatus with the cover removably secured to the chamber, and FIG. 8B showing the apparatus with the cover removed.

FIG. 8A illustrates the apparatus 50 in a non-use position, and FIG. 8B shows the apparatus 50 in a use position with the cover 52 removed for obtaining a test sample. The reagent containment system 60 in FIGS. 8A and B may be comprised of the same reagent combinations as illustrated in FIGS. 1–4, or may be any other combination of reagents and chemicals as desired for testing.

In use, the test apparatus is used by removing the heat-shrunk plastic seal 17 securing the cover 12 to the sample unit cylinder 14, and removing the cover 12, which cover has a premoistened swab 18 removably secured into the interior of the top 15 of the cover 12. After swabbing/sampling the affected area being tested, the cover 12 and swab 18 with the sample are re-inserted into the sample unit cylinder 14. The sample unit cylinder 14 has three indicator markings 22 on its exterior surface. When the cover 12 with swab 18 is re-inserted into the sample unit cylinder 14, it is moved downwardly longitudinally to the second mark, and the cover is twirled twice, breaking into the first containment unit 30 with Reagent A 36. The cover 12 is then moved downwardly longitudinally to the third mark and twirled twice more, breaking into the second containment unit 32 with Reagent B 38. The plunger is then depressed fully in a downwardly longitudinal manner, breaking into the bottom chamber 34 with Reagent tablet C, and is then twirled, moistening the reagent tablet C 42 at the bottom of the microtube test unit 16. The cover 12 with swab 18, having all three reagents thereon and mixed with the sample on the swab, is withdrawn upwardly and longitudinally into the sample unit cylinder 14.

The microtube test unit 16 is then detached, if desired, from the sample unit cylinder 14 at break point 26 by means of the finger grips 24. After removing the adhesive-backed aluminum foil seal 20, the microtube test unit 16 is then covered with the adhesive cap 20 and counted, such as by a luminometer 44 (see FIG. 5). To ensure proper reacting of all samples, the semi-rigid plastic sample unit cylinder may also be squeezed by hand.

After testing, the entire apparatus 10 may be easily disposed of. Further, before use, the entire test apparatus 10 may be easily carried and stored in the user's pocket or a portable, lightweight carrying case. The unique single use sequential unit dose containment system 49 within the microtube test unit 16 allows for easy storage and portability, without mixing of the reagent chemicals and possible spoilage of the chemicals therein.

The following examples are provided to illustrate optional uses of the sample and test kit apparatus and method:

EXAMPLE 1

Total Hygienic Test—Total sanitation ATP monitoring test kit: Pocket Swab™, (a trademark of Charm Sciences, Inc., Malden, Mass.). The swab contains water or cleaning solution (e.g. detergent, such as an anionic-like sodium lauryl sulfate, a non-ionic like Triton X-100, a quaternary ammonium like benzalkonium chloride at 0.01–0.3%, for swabbing biofilm and dried microbial film.

The chamber's ingredients are Buffer A: (0.1–0.3 ml) buffer containing phosphoric acid 0.05% and anionic detergents (0.1%) for rapid release of ATP from microorganisms. The buffers could be acids: e.g., trichloroacetic acid or phosphoric acid at 0.01–0.5%, pH 1–3 (e.g. 0.1% phosphoric acid pH 2 and 0.5% Triton X-100), or neutral to alkaline pH buffers such as tris, tricine or carbonate. Detergents can be anionic (sodium lauryl sulfate), neutral (Triton X-100) or cationic (like quaternary ammonium).

The indicator dye: pH indicator such as phenol red (PR) or bromocresol purple (BCP) at 0.0001–0.001%, just enough to be visible to the naked eye. The BCP is yellow in Buffer A, it changes to blue in Step 2 when B and A are mixed, and remains blue in Step 3 when A and B are mixed with Reagent C.

Buffer B is comprised of a neutralizer buffer to optimize the luciferin-luciferase reaction, e.g. 0.05–0.2M of tris, tricine or other biological buffers. Optionally, it is possible to combine Buffer A with Buffer B.

Tablet C contains luciferase and luciferin substrate for detection of ATP. These ingredients are stabilized in a tablet format (see U.S. Pat. Nos. 4,239,745, 4,239,852, 5,200,311, 5,283,180, 5,354,663, and 5,374,535, incorporated herein by reference).

EXAMPLE OF RESULTS ENCLOSED AS APPENDIX 1 Sanitation results (RLU) vs. the presence of various microorganism on surfaces in a processing food plant.

The swab can be dry for sampling wet surfaces, or is moistened with water/buffer for meat products and solid dairy products, like cheese.

APPENDIX 1

Table Example of results for the Pocket Swab in processing food plant

| LOCATIO # | Sanitation level | PocketSw ATP (RLU) | SPC CFU | YEAST CFU | MOLD CFU | COLI CFU | Total microbia CFU |
|---|---|---|---|---|---|---|---|
| 1 | Good | 0 | 0 | | | 0 | 0 |
| 2 | Good | 0 | 140 | 6 | 0 | 0 | 146 |
| 3 | Good | 0 | 0 | 0 | 0 | 0 | 0 |
| 4 | Good | 0 | 0 | 0 | 4 | 0 | 4 |
| 5 | Good | 0 | 0 | 0 | 0 | 0 | 0 |
| 6 | Good | 0 | 0 | 0 | 0 | 0 | 0 |
| 7 | Good | 0 | 0 | 0 | 0 | 0 | 0 |
| 8 | Good | 0 | 0 | 0 | 0 | 0 | 0 |
| 9 | Good | 0 | 0 | 0 | 0 | 0 | 0 |
| 10 | Good | 0 | 20 | 2 | 3 | 0 | 25 |
| 11 | Good | 0 | 0 | 0 | 0 | 0 | 0 |
| 12 | Good | 0 | 0 | 0 | 0 | 0 | 0 |
| 13 | Good | 0 | 0 | 0 | 0 | 0 | 0 |
| 14 | Good | 0 | 0 | 0 | 0 | 0 | 0 |
| 15 | Good | 0 | 0 | 0 | 0 | 0 | 0 |
| 16 | Good | 0 | 0 | 0 | 0 | 0 | 0 |
| 17 | Good | 0 | 0 | 0 | 0 | 0 | 0 |
| 18 | Good | 0 | 0 | 0 | 0 | 0 | 0 |
| 19 | Good | 0 | 10 | 0 | 0 | 0 | 10 |
| 20 | Good | 0 | 0 | 0 | 0 | 0 | 0 |
| 21 | Good | 0 | 0 | 0 | 0 | 0 | 0 |
| 22 | Good | 0 | 10 | 0 | 0 | 0 | 10 |
| 23 | low | 594 | 50 | 0 | 0 | 0 | 50 |
| 24 | low | 647 | 10 | 16 | 4 | 0 | 30 |
| 25 | low | 1347 | 210 | 8 | 0 | 0 | 218 |
| 26 | low | 2292 | 110 | 0 | 0 | 10 | 120 |
| 27 | low | 2437 | 388 | 0 | 0 | 0 | 388 |
| 28 | low | 2969 | 100 | 0 | 0 | 0 | 100 |
| 29 | low | 3267 | 2440 | 23 | 1 | 0 | 2464 |
| 30 | low | 3959 | 0 | 0 | 0 | 0 | 0 |
| 31 | low | 3989 | 0 | 0 | 0 | 280 | 280 |
| 32 | low | 4460 | 0 | 0 | 0 | 975 | 975 |
| 33 | med | 4889 | 13000 | 5 | 0 | 24 | 13029 |
| 34 | med | 6697 | 30 | 15 | 0 | 0 | 45 |
| 35 | med | 6975 | 13000 | 0 | 0 | 26 | 13026 |
| 36 | med | 7174 | 580 | 8 | 32 | 36 | 656 |
| 37 | med | 7275 | 10 | 123 | 10 | 0 | 143 |
| 38 | med | 8075 | 460 | 101 | 72 | 0 | 533 |
| 39 | med | 10625 | 190 | 0 | 52 | 0 | 242 |
| 40 | med | 10972 | 180 | 2 | 4 | 0 | 186 |
| 41 | med | 15830 | 300 | 187 | 2 | 0 | 489 |
| 42 | med | 28067 | 30 | 9 | 164 | 32 | 235 |
| 43 | med | 32009 | 3900 | 0 | 0 | 2 | 3902 |
| 44 | med | 42685 | 112 | 0 | 3 | 0 | 115 |
| 45 | high | 53712 | 6500 | 650 | 455 | 17 | 7622 |
| 46 | high | 59019 | 19500 | 0 | 1300 | 0 | 20800 |
| 47 | high | 130837 | 16250 | 520 | 178 | 46 | 16994 |
| 48 | high | 175154 | 19000 | 0 | 6500 | 0 | 26000 |

SPC — standard plate count for total aerobic bacteria
CFU — colony forming unit
COLI — coliforms bacteria
ATP — adeninenucleotide triphosphate
RLU — relative light unit

EXAMPLE 2

Testing residual raw milk/meat/fish. This test measures the activity of phosphatase as indicative of raw tissue, milk or serum in cooked produce (e.g. pasteurized milk, cooked meat salami, cold cuts, smoked fish). It also can be used to detect cross-contamination from raw material in processing surfaces and equipment intended for finishing products.

Commercial name—CHEF Test™ (a trademark of Charm Sciences, Inc., of Malden, Mass.). ALK Test™, Cross-contamination test.

The chamber ingredients include in Chamber A, a water or saline buffer, pH 6–10 with preservatives (e.g. benzoic acid, sorbate), and a pH indicator such as phenol red at 0.001%.

The second chamber contains tablet MP, with Tropix phosphatase substrate (CSPD, a product of Tropix, Massachusetts), freeze dried and made into a tablet.

Chamber 3 contains a stopping solution (0.0025–0.025M EDTA, 0.05–0.2M Tris base or other biological buffers, 0.1–0.3 NaCl, pH 8–11).

EXAMPLE OF RESULTS AS ENCLOSED IN APPENDIX 2 Study of CHEF Test™ Performance in testing cooked ground beef hamburgers.

APPENDIX 2

Study of CHEF Test™ Performance in Heat Processing of Ground Beef

Purpose

To demonstrate the CHEF (Cooking Heat Efficiency) Test™'s performance, precision and accuracy in predicting doneness of cooked ground beef. Inadequate cooking has been the major cause of stomach poisoning from pathogenic bacteria like *E.coli* and *salmonella*.

Introduction

The CHEF Test™ uses the presence of phosphatase activity to determine whether cooked meats have met CFR specified cooking temperatures. Acid phosphatase as an indicator for cooking has been reported in previous literature.

Principle

The CHEF Test™ uses a chemiluminescent substrate for rapid determination of phosphatase activity. The procedure includes the sampling step, which includes using a wet swab to sample the core of the meat (after splitting the meat sample to expose the inner core). Also, it can be used to swab an equipment surface (e.g., a slicing machine), or other surfaces to test for residual raw meat/milk. In the incubation step, the swab is brought into contact with the chemiluminescent substrate, e.g., CSPD, a Tropix product, for one to ten minutes at a temperature range from room temperature to 65° C., for example, 55° C. for one minute. At the reading step, the reaction is terminated and stabilized by adding a stopping solution and immediately counting relative light units (RLU) using a luminometer.

Results

The average CHEF Test™ for raw beef is in the range of 15,000 to 20,000 RLU, while fully cooked beef gives results in the range of 0–300 RLU (see Table 3). Results for ground beef heated to various temperatures and hold times are listed in Table 2.

Discussion

Using the results for fully cooked meat, a cut off for determining incompletely cooked meat can be set at the upper range (e.g. 300 RLU). In our field samples (Table 3) all the hamburgers were properly cooked (all results below 300 RLU). In our own cooking experiment, (Table 2), we effectively screen low temperature cooked products (Samples 1–4) from adequately processed and cooked products (Samples 5 and 6).

Conclusion

The CHEF Test accurately detects raw meat and also can distinguish fully cooked meats from incompletely cooked meats. Meat processed at a temperature 2° C. below CFR specifications and for thirty seconds too short a time (Sample 4), was identified as positive in this study. Samples properly processed, and hamburgers purchased from a local restaurant, were negative for residual raw meat.

TABLE 2

APPENDIX 2

CHEF Test results (RLU) of various ground beef samples held at various temperatures and times.

| Temp. °C. (°F.)<br>Hold Time –>:<br>Replicate # | Sample #1<br>53 (128)<br>60 sec.<br>RLU | Sample #2<br>57 (135)<br>60 sec.<br>RLU | Sample #3<br>59 (138)<br>60 sec.<br>RLU | Sample #4<br>63 (145)<br>60 sec.<br>RLU | Sample #5<br>65 (149)<br>60 sec.<br>RLU | Sample #6<br>69 (156)<br>16 sec.<br>RLU |
|---|---|---|---|---|---|---|
| #1 | 10536 | 12490 | 11622 | 2795 | 10 | 123 |
| #2 | 17784 | 22940 | 5481 | 3903 | 0 | 0 |
| #3 | 14325 | 8411 | 5040 | 2113 | 0 | 0 |
| #4 | 11979 | 6309 | 17881 | 2060 | 0 | 0 |
| #5 | 21310 | 12832 | 10475 | 4969 | 186 | 0 |
| #6 | 21426 | 6264 | 11022 | 5766 | 188 | 227 |
| Average | 16227 | 11541 | 10254 | 3601 | 64 | 58 |
| +/- Range | 4676 | 6285 | 4704 | 1542 | 95 | 96 |
| % activity | 95 | 68 | 60 | 21 | 3.8 | 3.4 |

TABLE 3

A dozen hamburgers purchased at a local food chain tested on the CHEF Test are reported in Table 3.

CHEF Test (RLU) of Hamburgers from Restaurant

| Hamburger # | CHEF (RLU) | Hamburger # | CHEF (RLU) |
|---|---|---|---|
| 1 | 0 | 7 | 37 |
| 2 | 0 | 8 | 0 |
| 3 | 0 | 9 | 0 |
| 4 | 0 | 10 | 0 |
| 5 | 0 | 11 | 0 |
| 6 | 0 | 12 | 0 |

EXAMPLE 3

Chemical and antibiotic residue test—Testing of residual antibiotics in milk, urine, and meats.

The swab is dry for sampling of water, milk, meat serum or urine.

The chamber ingredients are comprised of water or 0.005–0.1 phosphate buffer pH 5–8 in Chamber One. In Chamber Two, the tablet contains dried microorganisms, such as naturally luminescent bacteria such as *P. phosphoreum*, (Canadian Pat #1103050) or, genetically modified bacteria (e.g. *E.coli* mutant used in the Toxi-Chromotest EBPI, Ontario, Canada); a growth and maintenance nutrient (see U.S. Pat. No. 354,663 incorporated herein by reference), and a growth or activity indicator like chromogen, which in the presence of an enzyme, such as D-galactosidase or phosphatase, can produce color or luminescence (e.g., Tropix luminescence substrates: CSPD, Galacton-Plus).

Chamber Three contains an enhancing reagent, such as fluorescamine or Tropix enhancing reagents (Emerald, Sapphire).

The procedure for this test comprises obtaining a test sample with the probe means, inserting the swab into the buffer compartment, inserting the swab into the buffer compartment, inserting it into the tablet compartment, and the inserting the swab into the chromogen. It should be noted that the tablet and chromogen car be contained in a single compartment.

The test samples should be incubated for 1–120 minutes and the luminescence then recorded. Inhibition of luminescence indicates the presence of a chemical inhibitor in the sample. For example, using *E.coli* and Tropix Galacton-plus substrate in E*Colite/*ColiGel*™ media (a trademark of Charm Sciences, Inc., of Malden, Mass. ), can be used to detect antibiotics such as quinolones, and others. Using Bacillus stearothermophius, a variety of antibiotics can be detected in about 60–120 minutes using color change or change in luminescence substrate.

Each test kit is fully packaged all in one device, including the reagents, which greatly simplifies the test, making it user-friendly. The test utilizes simple steps which are controlled by the plunger and indicator marks, and has puncturable seals, such as aluminum foil seals, that separate the various compartments. It eliminates the need to prepare reagents, and no pipettes or dispensers are needed. This device eliminates operational mistakes due to inaccurate pipettes. Since all the reagents, liquid and tablets, are individually packaged and sealed, under optimum conditions, the test kit has excellent shelf life stability, with an expectation of over two month's stability at room temperature. The test device can be easily carried and used in any place, for example, in a processing plant, without restrictions.

Thus, the test apparatus of the invention provides for a safe, convenient, lightweight and inexpensive test apparatus that may be stored for longer periods and easily transported for use. Further, the invention is easy, neat and convenient to use. The prepackaged single use sequential unit dose containment system allows for fewer user errors in preparing reagent chemicals for use. While the single use packaging system of the invention is shown and described herein for the testing of ATP for sanitation purposes, it is recognized that the apparatus, system and method may be used for a wide variety of product applications.

What is claimed is:

1. A glass-free test apparatus for the bioluminescent detection of a ATP in a test sample, from or on a material, which apparatus consists essentially of:
    a) an elongated tubular sample unit having:
        i) a probe means having a first and second end, with said first end to obtain a test sample in use to be collected from or on a material;
        ii) an ATP sterile chamber having a first and second open end, and adapted to receive and retain therein, prior to use and after use, said probe means and having a cover for said first end of said chamber; and
        iii) threadable means to move longitudinally, said first end of said probe means within said chamber prior to use to selected sequential non-use, use and non-use positions; and
    b) a tubular test unit longitudinally aligned and attached to the second end of the chamber having:
        i) a reagent transparent housing with a bottom and having a first end and second closed end, said first end attached to said second open end of said chamber, said transparent housing composed of a transparent material adapted for use with or in a test instrument for the identification of the ATP in test sample by measurement of luminescence; and
        ii) ATP test sample reagent means to contact the test sample on said probe means and comprising a reagent package which comprises a plurality of separate, aligned, sealed compartments, which includes an ATP release or buffer solution with an indicator dye compartment and a separate luciferin-luciferase compartment, the compartments characterized by a plurality of separate, puncturable membranes adapted to be penetrated sequentially by the threadably controlled, longitudinal movement of said first end of the probe means, the test sample and the reagent means, in combination, providing a selected test for the detection of the ATP in the test sample, when the test sample and the reagent means are combined in said transparent housing in said test unit.

2. The apparatus of claim 1 wherein said test unit, said sample unit, and said sample unit cover are comprised of a disposable, transparent, semi-rigid, thermoplastic material generally cylindrical in shape.

3. The apparatus of claim 1 wherein the sample unit and test unit are longitudinally threadably, detachedly secured together.

4. The apparatus of claim 1 wherein said ATP test reagent means comprises a plurality of test reagents having at least one buffer test reagent with a pH indicator dye therein and a luciferase and luciferin substrate test reagent for detection of said test sample in the presence of the buffer and dye indicator.

5. The apparatus of claim 1 for the detection of ATP from a material or surface and wherein said first end of said probe means is pre-moistened and said reagent means comprises a plurality of test reagents to include:
    a) a buffer solution compartment with a detergent and an indicator dye, with optionally a neutralizing buffer solution compartment; and
    b) a tablet which, in the luciferin-luciferase compartment, comprises luciferase and a luciferin substrate for the detection of ATP in the sample.

6. In combination, the test apparatus of claim 1 and a luminometer as a test instrument to measure the bioluminescence in said test unit for the detection of said test sample.

7. The combination of claim 6 wherein said test unit is not detached and said test unit of the apparatus is placed in a luminometer measuring section for detection.

8. The apparatus of claim 1 which includes probe position identification means comprising a plurality of selected user-visual identification positions between said probe means and said chamber to identify the position of said probe means within said chamber.

9. A method for the detection of ATP by a user of a test sample from or on a material, in which said test sample is combined with ATP test reagents to provide test results, which method consists essentially of:
    a) providing an elongated, tubular, sterile, glass-free test apparatus with a sample unit constructed and arranged to obtain a test sample to retain a probe means having a probe end therein, and a transparent, closed end test unit at the one end to provide test results;
    b) removing said probe means and collecting the material to be tested to obtain a test sample on the probe means;

c) inserting said probe means within said test apparatus;

d) threadably, longitudinally moving said probe means in said test apparatus, with said test sample, sequentially between a starting non-use position with the probe end within the sample unit, a use position with the probe end in the test unit, and an ending non-use position with the probe end within the sample unit;

e) puncturing an ATP-packaged test reagent selected for the particular test method for the sample by the downwardly threadable longitudinal movement of the probe end of the probe means to rupture a plurality of membranes defining separate compartments having an ATP release-buffer solution with an indicator dye, and a luciferin-luciferase composition to provide a contacting of said ATP test reagent and said test sample from said probe means in said test unit; and f) determining the luminescence within said transparent test unit.

10. The method of claim 9 which includes measuring with a luminometer the amount of bioluminescence of said test sample within said test unit.

11. The method of claim 9 which includes providing a plurality of packaged ATP test reagents in said test unit having at least one buffer test reagent, with a pH indicator dye therein and a luciferase and luciferin composition test reagent for reacting with said test sample in the presence of the buffer and dye indicator.

12. The method of claim 9 wherein the test reagent comprises a plurality of test reagents to include:

a) a buffer solution compartment with a detergent and an indicator dye;

b) optionally a neutralizing buffer solution compartment; and c) a tablet compartment which comprises luciferase and a luciferin composition for the detection of ATP in the sample.

13. The method of claim 12 which includes placing said undetached test unit of the apparatus in a luminescent-measuring chamber of a luminometer.

14. A glass-free test apparatus for the bioluminescent determination of ATP in a test sample, which test apparatus consists essentially of:

a) an elongated tubular sample unit having:

i) a probe means having a first and a second end, with said first end comprising a premoistened swab to obtain a test sample;

ii) an ATP-sterile chamber having a first end and a second end and adapted to retain and receive, after obtaining the test sample, said probe means and having a cover for the first end, with the second end of the probe means attached thereto; and iii) threadable means to move longitudinally, said first end of said probe means within said chamber to selected, sequential non-use, use, and non-use positions; and b) a tubular test unit longitudinally aligned and attached to the second end of the chamber having:

i) a transparent housing with a closed bottom end adapted for use with a test instrument to measure emitted bioluminescence within the housing; and ii) ATP test sample reagent means, and comprising sealed reagents, in separate, sealed compartments characterized by a plurality of separate, aligned, swabs-puncturable membranes to include; a release solution for the release of the ATP in the test sample on the swab; a buffer solution with an indicator dye; and a luciferin-luciferase composition, the reagent means with the ATP-containing test sample on the swab combined in the bottom housing unit to provide for a bioluminescence ATP detection test.

15. The apparatus of claim 14 wherein the release solution and buffer solution are combined in a single membrane sealed reagent means compartments.

16. The apparatus of claim 14 wherein the luciferin-luciferase composition is in stabilized tablet form.

17. The apparatus of claim 14 wherein the release solution comprises an acidic solution and the buffer solution neutralizes the test sample release solution.

18. The apparatus of claim 14 wherein the release solution contains a visible dye.

19. A method for the bioluminescent determination of ATP in a test sample, which method consists essentially of:

a) providing a glass-free test apparatus with a sample unit having an enclosed ATP-sterile chamber and a top cover with a probe means of a premoistened swab at one end within the chamber, and a transparent test unit at an other end of the sample unit, and containing a plurality of separate, membrane-puncturable, sealed test reagent means;

b) removing the probe means from the sterile chamber;

c) collecting a test sample from a material or surface to be tested for sanitation;

d) inserting the swab with the test sample back into the sterile chamber;

e) threadably, longitudinally moving the cover with the swab and collected test sample in the sterile chamber, to puncture with the swab sequentially the plurality of membrane-sealed reagent means of a release solution and a buffer solution, and to permit the resulting admixed test sample with release solution and buffer solution, with a visible pH indicator, to contact a luciferin-luciferase composition, which provides a bioluminescent ATP test;

f) threadably, longitudinally removing the swab from the test unit; and g) measuring the amount of bioluminescence in the test unit to determine the amount of ATP in the test sample.

20. The method of claim 19 wherein the release solution is acidic and contains a visible, pH indicator dye, and the buffer solution is a neutralizing buffer solution, and the luciferin-luciferase composition comprises a stabilized luciferin-luciferase tablet.

21. The method of claim 19 which includes inserting the test unit undetached from the sample unit into a luminometer test instrument to measure the ATP bioluminescence.

22. The method of claim 19 which includes the swab with the test sample penetrating and sequentially rupturing a first, a second, and a third thin, rupturable seal membrane, which membranes extend radially, fully across the test unit, to define separate reagent means.

\* \* \* \* \*